United States Patent [19]

Coates

[11] Patent Number: 4,475,912
[45] Date of Patent: Oct. 9, 1984

[54] ADJUSTABLE DIAPERS WITH FASTENING MEANS

[76] Inventor: Fredrica V. Coates, 1608 Dublin Rd., Charlottesville, Va. 22903

[21] Appl. No.: 315,049

[22] Filed: Oct. 26, 1981

[51] Int. Cl.³ .............................................. A61F 13/16
[52] U.S. Cl. .................................... 604/385; 604/391
[58] Field of Search ................................ 604/386, 391

[56] References Cited

U.S. PATENT DOCUMENTS

| | | |
|---|---|---|
| D. 192,282 | 2/1962 | Newman . |
| D. 202,320 | 9/1965 | Van Every, Jr. . |
| D. 206,476 | 12/1966 | Cournoyer . |
| D. 209,181 | 11/1967 | Larson . |
| 999,820 | 8/1911 | Martin . |
| 1,280,821 | 10/1918 | O'Leary . |
| 1,382,042 | 6/1921 | Wright . |
| 2,251,626 | 8/1941 | Hertzberg . |
| 3,081,772 | 3/1963 | Brooks et al. . |
| 3,089,494 | 5/1963 | Schwartz . |
| 3,141,461 | 6/1964 | Farris . |
| 3,150,664 | 9/1964 | Noel . |
| 3,256,545 | 6/1966 | Lewis, Jr. et al. . |
| 3,359,980 | 12/1967 | Rosenblatt . |
| 3,470,575 | 10/1969 | Larson et al. . |
| 3,554,195 | 1/1971 | Murdoch . |
| 3,618,608 | 11/1971 | Brink . |
| 3,653,381 | 4/1972 | Warnken . |
| 3,763,515 | 10/1973 | Voss . |
| 3,955,575 | 5/1976 | Okuda . |
| 3,994,040 | 11/1976 | DiStefano . |
| 4,051,854 | 10/1977 | Aaron . |

Primary Examiner—C. Fred Rosenbaum
Assistant Examiner—Sherri E. Vinyard
Attorney, Agent, or Firm—Lowe, King, Price & Becker

[57] ABSTRACT

A diaper (10) according to the invention comprises an absorbent washable fabric (12) prefolded into rectangular multi-ply form with opposite inner and outer surfaces (15, 16). The fabric includes a pair of side panels (20) which can be folded inwardly flush on the fabric inner surface (15) to increase absorbency and give the diaper (10) a substantially hourglass configuration to fit the profile of an infant. A pair of attachment tabs (35) each secured to an upper corner of the fabric (12) engage fastening strips (40) secured to the outer surface of the fabric (12) adjacent a lower edge (42) thereof. The fastening strips (40) are vertically oriented for adjustable, mating engagement with the attachment tabs (35) to accommodate growth of the infant. A transverse edge portion of (42) the fabric (12) can be folded along a fold line (L) to provide a smaller diaper for newborn infants, and fastening means (45) is provided to enable gradual expansion of the diaper as the infant grows. A device (50) for removing lint from the strips (40) or tabs (35) is also disclosed. The device (50) includes a handle (52) and needle-like projections (54) attached to the handle. The projections (54) are slidable under the barbed or loop-like projections of the tabs (35) or strips (40) to remove the lint.

13 Claims, 9 Drawing Figures

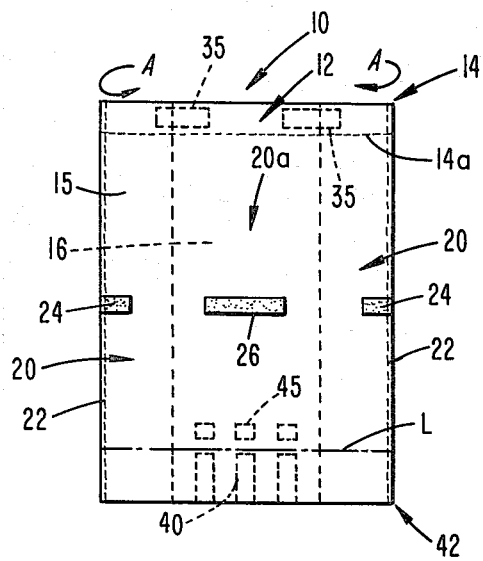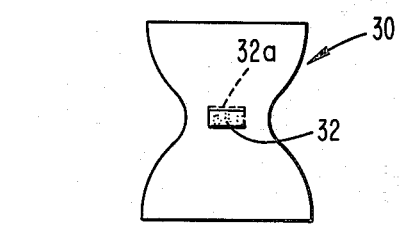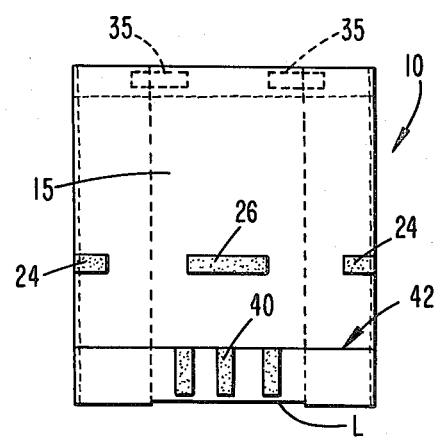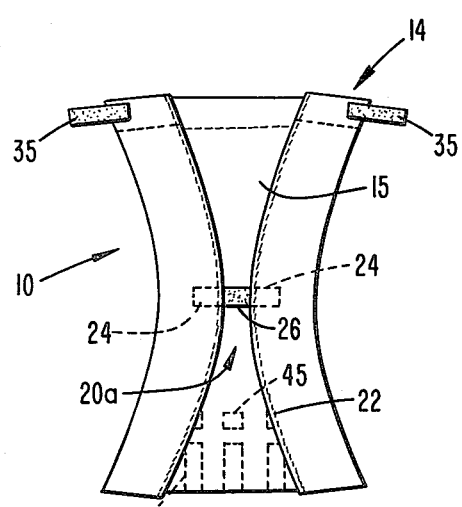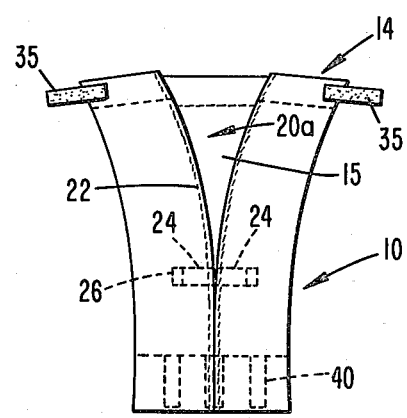

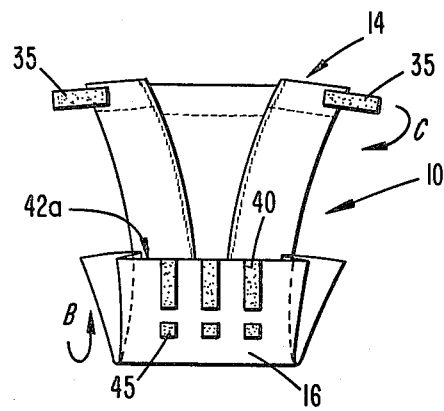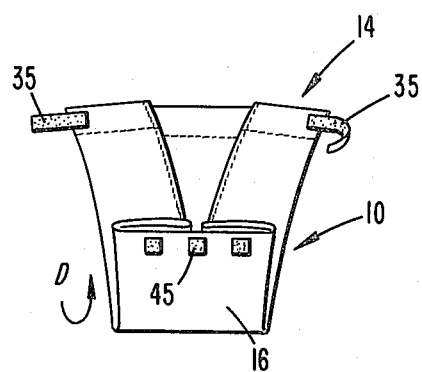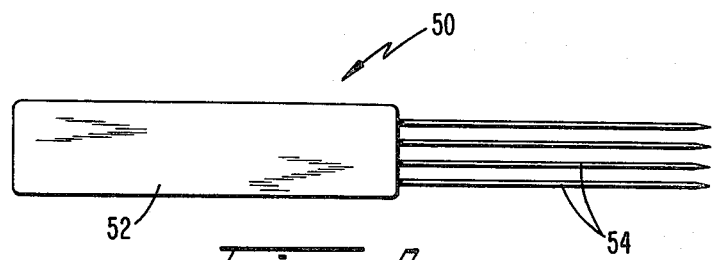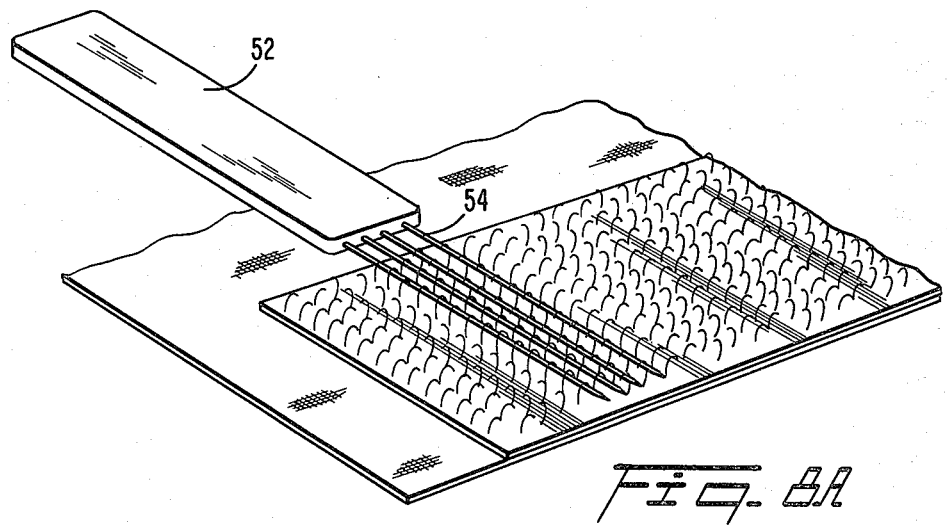

ADJUSTABLE DIAPERS WITH FASTENING MEANS

TECHNICAL FIELD

This invention generally relates to diapers and fastening means therefor, and more particularly, to washable diapers having a novel fastening arrangement that enables the diaper to adapt to infant growth.

BACKGROUND ART

Washable diapers for infants basically include a folded cloth or other absorbent material positioned between the legs and fastened about the waist to contain and draw moisture away from the infant's skin. Such diapers are typically supported to the infant with safety pins piercing the diaper ends. The pins, however, can inadvertently open and pierce the skin, or possibly be swallowed by the infant. In addition, the use of pins requires fine motor control and good visual coordination and can therefore be only applied with difficulty by handicapped or blind persons.

Other types of fastening means, such as "Velcro" tape having resiliently deformable projections or pressure sensitive adhesive material, have been affixed to washable diapers and tend to avoid some of the problems previously extant with safety pins. Such diapers employing other aforesaid fastening means appear to allow the diaper to "grow" to accommodate infant growth, however, these types of diapers of which I am aware do not appear capable of swaddling newborn infants of approximately eight to eleven pounds, and thereafter of expanding to accommodate larger infants. Accordingly, at least two separate sizes of diapers are typically required.

In washable diapers employing "Velcro" fastening tapes, frequent washing tends to cause excessive lint buildup that tends to deteriorate the adhesive effect of the tape and diaper efficiency. To my knowledge, there is no effective means for removing the lint from the tape to maintain desired adhesive conditions.

It is accordingly an object of the present invention to provide an improved diaper which can be worn by newborn infants and thereafter expand to accomodate infant growth.

A further object is to provide a lint removing device capable of removing lint from adhesive tape carrying resiliently deformable projections to improve diaper efficiency.

Yet another object is to provide a diaper that can easily be applied to infants under poor light conditions, and that is capable of easy application by blind or handicapped persons.

In diapers of which I am aware that accommodate infant growth, positioning of the fastening means allows expansion about only the waist area and does not appear to be capable of longitudinal expansion to accommodate increased infant height or leg growth.

Another object of the invention, therefore, is to provide a new and improved diaper that is capable of expansion to accommodate increased infant height in addition to waist and leg expansion.

Still a further object is to provide a diaper which retains moisture away from the infant's skin.

Still another object is to provide a diaper that is comfortable to the infant and can be secured in a rapid and easy manner.

A still further object of the invention is to provide a diaper and releasably attachable absorbent pad means and fastening means therefor for extra absorbency.

Handicapped adults and children exhibiting poor bladder control must often wear diapers. Such persons can usually change the diaper themselves; however, to my knowledge, there does not appear a diaper capable of fitting adults that includes characteristics allowing for rapid and easy change.

Another object of the invention is to provide a diaper that can be worn by adults or children and easily changed by the wearer.

DISCLOSURE OF THE INVENTION

A diaper, according to the present invention, comprises an absorbent washable fabric which extends around an infant's bottom to retain and draw moisture away from the skin. A pair of attachment tabs secured to an upper portion of the fabric engages attachment tab fastening means secured to the fabric outer surface away from the infant's skin. In wear position, such fastening means extends in a substantially vertical direction for adjustable, mating engagement with the tabs to accommodate increased infant height, in addition to waist and leg growth.

Such attachment tab fastening means preferably includes a plurality of attachment strips having resiliently deformable projections thereon. The strips extend from the lower edge portion of the fabric towards the crotch area. The inwardly directed edges of the strips can define a transverse fold line. Folding of the lower edge portion along the fold line towards the crotch area serves to hide the strips and shorten the diaper length to accommodate newborn infants. Second fastening means secured to the fabric outer surface adjacent an inwardly directed portion of the attachment strips is thereby exposed to engage the attachment tabs for swaddling the newborn infant.

A diaper insert and fastening means therefor is provided for flush positioning and attachment to the crotch area of the fabric inner surface for increased absorbency.

A lint remover for removing excessive lint buildup from the attachment strips is also provided. The remover includes a handle portion and a plurality of substantially rigid needle-like projections projecting outwardly therefrom. The pointed ends of the needle-like projections tend to catch and remove lint when reciprocated along the surface of the attachment strips.

Still other objects and advantages of the present invention will become readily apparent to those skilled in this art from the following detailed description, wherein I have shown and described only the preferred embodiments of the invention, simply by way of illustration of the best mode contemplated by me of carrying out my invention. As will be realized, the invention is capable of modifications in various obvious respects, all without departing from the invention. Accordingly, the drawings and description are to be regarded as illustrative in nature, and not as restrictive.

BRIEF DESCRIPTION OF THE DRAWING

FIG. 1 is a front plan view of the inner surface of the diaper in accordance with the present invention, showing the position of attachment and fastening means and location of the fold line in unfolded position;

FIG. 2 is a front plan view of the diaper with the side panels folded inwardly to thereby define crotch position and expose the attachment tabs for fastening;

FIG. 3 is a front plan view of a diaper insert and fastening means therefor for attachment to the crotch position of the diaper for extra absorbency;

FIG. 4 is a perspective view of the diaper in partially folded position showing the orientation of the fastening strips for engagement with the attachment tabs;

FIG. 5 is a front plan view of the diaper showing the lower edge portion thereof folded inwardly along the fold line to accommodate newborn infants;

FIG. 6 is a view similar to FIG. 5 showing subsequent folding of the side panels to cover the fastening strips for securing the diaper to newborn infants;

FIG. 7 is a front view of the diaper shown in FIGS. 5 and 6 illustrating location of the second fastening means for engagement with the attachment tabs for securing the diaper to newborn infants; and FIGS. 8 and 8a are respectively front and perspective views of a lint remover for use in removing lint material from the attachment tabs and fastening strips of the present invention.

BEST MODE FOR CARRYING OUT THE INVENTION

Referring to FIG. 1, diaper 10 of the invention is shown in unfolded position to include a sheet of washable fabric 12, such as thin weave cotton, which is preferably preformed by folding to double thickness to define a rectangular, multi-ply diaper form. The free edges extending tranversely along upper edge portion 14 of fabric 12 are overlapped and thereafter secured together with a continuous line of through stitching 14a. The stitching 14a extends parallel to the upper edge to maintain the basic rectangular fabric shape and further define corresponding inner and outer surfaces 15, 16 respectively provided on opposite sides of fabric 12.

A pair of side panels 20 extend lengthwise along lengthwise edge portions of fabric 12 for improved absorbency and thereby define a center panel 20a. Panels 20 are formed by folding the lengthwise portions to double thickness and reinforcing the fold line with through stitching 22 extending adjacent and parallel to the fold lines. As shown in FIGS. 1 and 2, side panels 20 can be folded inwardly to overlapping position flush on surface 15, in the direction indicated with arrows A. In such folded position, diaper 10 assumes an hourglass shape convenient for wrapping around the baby's bottom and assists in drawing moisture away from the infant's crotch and navel areas.

Panel fastening strips 24 are each secured to inner surface 15 on side panels 20 and extend transversely for attachment to a center panel strip 26 when the side panels are folded in the direction of arrows A. Each panel fastening strip 24 and the center panel strip 26 is secured to surface 15 with through stitching. Preferably, strips 24, 26 comprise resiliently deformable barbed projections and loop-like projections, respectively, such as male and female "Velcro" tape, to assure secure attachment conditions and withstand repeated washings without destroying the adhesive nature thereof. Strips 24, 26 extend transversely in coaxial alignment with each other to form the hourglass shape compatible for diapering infants, shown in FIG. 2. In folded position, side panels 20 prevent strips 24, 26 from contacting the infant's crotch area to assure comfortable wear. Of course, however, the invention is capable of use without side panels 20 and the strips 24, 26, through appropriate forming and padding of diaper 10 for shape and absorbency.

A diaper insert 30, formed of cotton weave or like material into a multi-ply, hourglass shape, can be positioned flush on inner surface 15 on center panel 20a prior to folding side panels 20 over the center panel (see FIG. 3). Insert 30 assists in improving the absorbency of diaper 10 and further includes a strip 32 carrying resiliently deformable barbed projections for attaching the insert to center panel strip 26. A strip 32a having resiliently deformable loop-like projections can be provided on the opposite side of insert 30 in corresponding location opposite strip 32 to receive the panel fastening strips 24, thereby securing side panels 20 in folded position flush on center panel 20a, as shown in FIG. 2. Alternatively, for improved absorbency, it will be appreciated that another one of diapers 10 can advantageously substitute for insert 30. As an insert, folding of side panels 20 of a second diaper 10 flush on outer surface 16 of center panel 20a serves to locate strips 24 in adjacent position in location corresponding to center strip 26, for secure attachment respectively to strip 26 and strips 24 provided on the first diaper.

To secure diaper 10 to the infant, a pair of attachment tabs 35, preferably having resiliently deformable barbed projections, such as male "Velcro" tape, is each secured to an upper corner of side panels 20 with through stitching. Each tab 35 projects laterally outward from upper edge porton 14 when side panels 20 are folded onto center panel 20a into folded position shown in FIG. 2.

Three of fastening strips 40 are provided on diaper 10 for mating engagement with tabs 35, and preferably contain resiliently deformable loop-like projections, such as female "Velcro" tape. Strips 40 are secured to outer surface 16 on center panel 20a with through stitching and extend longitudinally along lower edge portion 42 thereof, as shown in FIGS. 4 and 5, in spaced apart and parallel relationship to each other. In the preferred embodiment, fastening strips 40 are of the same length and extend inwardly towards the crotch portion of diaper 10.

A transverse fold line L, which can be coincident with the inwardly directed edge of each fastening strip, is provided as shown in FIG. 1. Fold line L, which can be imprinted on the diaper for easy identification, allows diaper 10 to be folded into smaller size for newborn infants, as discussed below.

Second fastening means, such as fastening squares 45 formed of resiliently deformable loop-like projections, such as female "Velcro" tape, is provided on outer surface 16 inwardly from fold line L. Each of squares 45 is secured to fabric 12 with through stitching in spaced, coaxial relationship with each of fastening strips 40. When lower edge portion 42 is folded along fold line L, as discussed infra, enabling diaper 10 to accommodate newborn infants, squares 45 advantageously serve to secure the diaper to the infant through engagement with attachment tabs 35, as will be seen more clearly below. Alternatively, the strips 40 can replace squares 45 by extending the strip length beyond fold line L.

The advantages derived through use of the unique design and novel arrangement of fastening means provided in diaper 10 is best understood and appreciated through a discussion of the steps involved in diapering infants. Prior to placing the infant on diaper 10, side panels 20 are folded into flush position on inner surface 15 over center panel 20a, as shown in FIG. 2. Previously, diaper insert 30 or another one of diapers 10 has been secured to surface 15 to overlap the center panel in the manner described above, if additional absorbency is required. Thereafter, the infant's bottom is then placed upon the center crotch portion of diaper 12 (see FIG. 2). Lower edge portion 42 is then brought upwardly in the direction of arrow B (FIG. 4), to cover the infant's abdominal area and thereby expose fastening strips and squares 40, 45 which advantageously do not contact the skin. Upper edge portion 14 extends around the infant's lower back area; thereafter, attachment tabs 35 are brought forwardly, in the direction of arrow C (FIG. 4), for secure attachment to the fastening strips or squares. Diaper fastening in this manner provides for a tighter bind around the legs to retain moisture, without causing discomfort to the wearer.

In the wear position described above, fastening strips 40 are vertically oriented to advantageously allow for adjustable positioning of tabs 35 on the strips to accommodate infants of different size or age. For example, attachment tabs 35 can be positioned on strips 40 adjacent lower edge 42a to diaper large or older infants who require increased diaper size. For smaller infants, tabs 35 advantageously contact portions or strips 40 located inwardly from edge 42a to reduce diaper size for comfortable and proper wear. Of course, depending on infant size, different ones of strips 40 can be engaged with tabs 35 in a rapid and easy fashion and at no time contact the infant's skin. The use of vertically oriented strips 40 tends to reduce the amount of attachment material necessary for diapering infants of all sizes, vis-a-vis horizontal strip placement. Preferably, strips 40 are approximately three to five inches in length. In view of the foregoing description, however, it will be appreciated that the diaper size varies inversely with the strip length. Therefore, a large strip allows the user to fold the diaper to smaller sizes.

Vertical placement of strips 40 also enables rapid and easy attachment of tabs 35 thereon. Less coordination is required, allowing for easy diaper changing under poor light conditions (e.g., nighttime). Blind or handicapped parents will also find diaper changing easy with the present invention.

Newborn infants are also advantageously fitted with the same diaper 10 in the following manner. Prior to placing the newborn infant on the diaper, lower edge portion 42 is folded inwardly flush on surface 15 along fold line L into position shown in FIG. 5. Although such folding exposes fastening strips 40, side panels 20 are thereafter folded into flush position on center panel 20a thereby concealing strips 40 to prevent contact with the baby's skin (see FIG. 6). It will be appreciated that a much smaller diaper 20 with increased absorbency is thereby provided for the newborn infant in comparison with the diaper shown in FIG. 2 which accommodates larger or older infants, as discussed above.

After folding side panels 20, as shown in FIG. 6, the baby is placed upon the smaller diaper and the lower diaper portion is raised upwardly in the direction of arrow D (see FIG. 7) to cover the baby's abdominal area, as discussed in connection with the larger diaper of the invention. In raised position, fastening squares 45 or extended portions of strips 40, discussed supra, are now exposed outwardly from the baby. Attachment tabs 35 are then brought forward into engagement with one of squares 45 to complete diapering. Since three of squares 45 are provided at laterally spaced intervals, it will be appreciated that the adjustable nature of the diaper is maintained to accommodate different sizes of newborn babies by appropriately positioning the tabs on the squares.

To provide additional adjustability of diaper 10, barbed and loop-like projections are respectively provided on opposite surfaces of tabs 35 (see FIG. 6), enabling each tab to be folded into overlapping relationship to reinforce the tab and shorten the tab length. This feature is particularly useful when diaper 10 is folded to smaller sizes, since the tabs can now overlap and securely fasten to each other in flush engagement without leaving the free ends of the tabs unsecured.

Frequent washing of diaper 10 tends to cause excessive accumulation of lint and other foreign material in the resiliently deformable barbed (e.g. male "Velcro") or loop-like projections of tabs 35 or strips 40, which tends to reduce the adhesive nature of the tabs. Therefore, for the purpose of removing lint, especially from the loop-like projections (e.g. female "Velcro"), a lint removing device 50 is provided.

As shown in FIG. 8, device 50 includes a handle portion 52, formed preferably from wood or plastic. A plurality of needle-like projections 54, either embedded in or glued to handle 52, project outwardly from the handle a uniform distance of preferably three-fourths inch.

In operation, device 50 is used by sliding the tips of needles 54 along the surface of the tabs under the loops, as shown in FIG. 8a, together with a lifting motion. As the needles penetrate surface lint, the Velcro loops tend to yield to the needle tips to enable the lint particles to be efficiently lifted away from the tab surface for disposal.

For best results, it is preferable to hold the tab or other surface being cleaned with the fingers of one hand in order to see the loops and direct the needle tips under the loops with the fingers of the other hand. Such hand held control is especially important to prevent the needles from penetrating the surface and to properly direct the tips.

In the preferred embodiment, four needles 54, preferably formed from steel, are secured to handle 52 and are spaced apart parallel to each other approximately one thirty-second inch to one sixteenth inch. If a greater number of needles are used, problems with controlling needle direction arise. Fewer needles clear less surface area and therefore require additional time for effective lint removing operation.

Needles 54 must be thin enough to fit through the loops, while retaining flexibility and strength for proper control and to prevent the needles from bending or breaking during the aforesaid lint removing action. The aforesaid spacing between needles 54 assures positive and accurate control to achieve uniform cleaning.

In this disclosure, there are shown and described only the preferred embodiments of the invention, but, as aforementioned, it is to be understood that the invention is capable of changes or modifications within the scope of the inventive concept as expressed herein. For example, while the present invention has been described to prefer the use of resiliently deformable barbed and loop-like projections, such as "Velcro", for forming the tabs and strips, it will be understood that other adhesive means can also be utilized within the scope of the present invention. Also, diaper 10 of the invention can be suitably sized for use by handicapped persons or persons having poor bladder control. During manufacture of diaper 10, the diaper fabric is preferably preshrunk prior to securing tabs 35, strips 40, squares 45, and attachment portions 24, 26 thereto. Of course, the diaper material should be appropriately textured to prevent diaper rash.

I claim:

1. A diaper, comprising:
   (a) absorbent material having opposite inner and outer surfaces, said inner surface adapted to face a wearer to be diapered;
   (b) attachment means secured to an upper portion of the fabric;
   (c) first fastening means secured to the outer surface of the fabric adjacent a lower edge portion thereof, said first fastening means extending longitudinally from the lower edge portion for engagement with the attachment means to secure the diaper to a wearer;
   (d) second fastening means secured to the outer surface of the fabric and spaced inwardly from the first fastening means, said second fastening means engageable with the attachment means to shorten diaper length and thereby accommodate growth of the wearer;
   (e) a pair of side panels integrally formed by overlapping side portions of the fabric into a folded position on said outer surface; and
   (f) panel attachment means for fastening the side panels to an intermediate portion of the inner surface to insulate said panel attachment means from the wearer; wherein said attachment means includes a pair of attachment tabs and said fastening means includes a plurality of elongated fastening strips, each strip having an inwardly directed edge defining a transverse fold region to allow a lower edge portion of said diaper fabric to be folded along the fold region on the fabric inner surface prior to folding the side panels, thereby shortening the length of the diaper fabric to accommodate newborn infants and prevent contact between the infant and the first fastening means.

2. A diaper according to claim 1, wherein said second fastening means is engageable with the attachment tabs when the fabric is folded along the fold region to diaper a newborn infant, said second fastening means extending along the fabric outer surface inwardly from the fold region, thereby being exposed to the attachment tabs while said fastening strips remain insulated from the wearer's skin.

3. A diaper according to claim 2, wherein said fastening strips are formed of material having one of resiliently deformable barbed or loop-like projections and said attachment tabs are formed of material having one of resiliently deformable barbed or loop-like projections adapted to mate with the fastening strips.

4. A diaper according to claim 3, wherein said fastening means includes a plurality of substantially parallel strips of substantially equal length and spaced apart from each other to thereby accommodate increased infant growth about the girth.

5. A diaper according to claim 4, wherein said second fastening means includes a substantially square portion of material having resiliently deformable projections secured inwardly adjacent at least one of the fastening strips.

6. A diaper according to claim 5, wherein each of said fastening strips and square portions is secured to the fabric with through stitching.

7. A diaper according to claim 6, further comprising a diaper insert adapted to be positioned flush on the fabric inner surface to thereby increase absorbency of the diaper, said insert including insert fastening means positioned correspondingly on opposite surfaces of the insert to thereby engage the panel attachment means.

8. A diaper according to claim 7, further comprising a lint removing device including a handle portion and a plurality of needle-like projections projecting outwardly therefrom, said projection having free ends being slideable through the resiliently deformable barbed or loop-like projections to thereby remove lint or foreign matter therefrom.

9. A diaper according to claim 3, wherein said attachment tabs have opposite surfaces carrying respectively resiliently deformable barbed projections and resiliently deformable loop-like projections.

10. A pinless, absorbent diaper, comprising:
    (a) an absorbent material having an inner surface adapted to contact a wearer and an outer surface;
    (b) first fastening means secured to an upper portion of said material;
    (c) second fastening means secured to the outer surface of the material adjacent a lower edge portion thereof immediately below a fold region and adapted to couple to the first fastening means to form a diaper having a first effective size;
    (d) a lower portion of the material carrying the second fastening means foldable along the fold region to reduce an effective length of the diaper;
    (e) inwardly foldable side flaps on opposite sides of the diaper to reduce an effective width of the diaper; and
    (f) third fastening means secured to the outer surface of the material immediately above the fold region and adapted to couple to the first fastening means, with said lower portion of the material folded along the fold region and with the side flaps folded inwardly to form a diaper having a second effective size smaller than the first effective size, the inwardly folded side flaps insulating the second fastening means from the skin of the wearer.

11. In a diaper comprising an absorbent washable material having an inner surface adapted to contact a wearer and having an outer surface, first fastening means secured to an upper portion of said material and second fastening means secured to a lower region of the outer surface of the material, said second fastening means having a lower portion adjacent an edge of the material and having an upper portion, a fold region being established between the upper and lower portions of said second fastening means:
    a folding method comprising the steps of folding the material inwardly along the fold region between the upper and lower portions of said second fastening means, folding side portions of the material toward a central portion of the material to cover the lower portion of the second fastening means and coupling the upper portion of said second fastening means to said first coupling means to form a folded diaper sized to fit a newborn infant.

12. A method of securing a diaper to a newborn infant, said diaper including a piece of generally rectangular, absorbent material, first fastening means affixed to an upper portion of the material and second fastening means affixed to a lower portion of the material and adapted to couple to the first fastening means when the diaper is secured to the infant, comprising the steps of:

folding the absorbent material along a transverse fold region to reduce the effective length of the diaper;

folding side panels of the absorbent material toward a central portion of the material to reduce the effective width of the diaper; and coupling the first fastening means to the second fastening means such that a portion of the second fastening means is exposed and faces away from the infant.

13. A method of securing a diaper to a newborn infant, the diaper including a piece of generally rectangular, absorbent material, first fastening means affixed to an upper portion of the material and second fastening means affixed to a lower portion of the material and adapted to couple to the first fastening means when the diaper is secured to the infant, comprising the steps of:

folding a lower portion of the diaper inwardly to establish a region of double thickness of the absorbent material;

folding opposite side panels of the diaper inwardly onto the region of double thickness to establish a region of quadruple thickness;

positioning the quadruple thickness portion of absorbent material on the infant's abdomen, to absorb moisture; and coupling the first fastening means to the second fastening means to form a folded diaper of a reduced length and width that is sized to fit a newborn infant.

* * * * *